United States Patent [19]

Somes et al.

[11] Patent Number: 5,108,578

[45] Date of Patent: Apr. 28, 1992

[54] PH AND CONCENTRATION METER

[75] Inventors: Loren Somes, Haverhill; Thomas Paquette, Shrewsbury; Laura Brockway, Charlestown; Paul Sydlowski, Wakefield; Steven West, Hull; Chin-I Shyr; Christopher McIntre, both of Newton; Jeffrey S. Cohen, Wilmington; James Barbookles, Malden, all of Mass.

[73] Assignee: Orion Research, Inc., Cambridge, Mass.

[21] Appl. No.: 521,731

[22] Filed: May 10, 1990

[51] Int. Cl.⁵ .............................................. G01N 27/26
[52] U.S. Cl. .................................... 204/433; 204/400; 204/406; 204/407
[58] Field of Search ................. 204/400, 406, 407, 433

[56] References Cited

U.S. PATENT DOCUMENTS

| 3,902,982 | 9/1975 | Nakagawa | 205/406 |
|---|---|---|---|
| 4,090,925 | 5/1978 | Jungman | 204/433 |
| 4,225,410 | 9/1980 | Pace | 204/406 |
| 4,912,417 | 3/1990 | Gibboney et al. | 204/406 |

*Primary Examiner*—John Niebling
*Assistant Examiner*—Bruce F. Bell

[57] ABSTRACT

The present invention comprises an electrochemical metering apparatus that provides for convenient storage and presentation of the analytical electrode, simple assembly, and two calibration modes. The apparatus includes an electrode storage and presentation assembly that permits the user to introduce the electrode into a sample solution while simultaneously observing the meter's output, and store the electrode when not in use. All structural components are intended to fit together with interlocking tabs and windows. A serial port fits within the construction of the main housing without the need for bolts, and battery clips that depend directly from the circuit board obviate the need for wiring connections. The present invention also features two calibration modes. A "segment addition" mode permits separation of the voltage/concentration curve into individually plotted regions, the number of which depends on the number of reference solutions used in the calibration procedure. The segment corresponding most closely to the measured potential of a sample solution is used to calculate concentration. In an alternative calibration mode, one or more reference solutions are used to establish meterd voltage/concentraiton combinations that are compared with expected, known values. Any discrepancies therebetween furnish a "noise level" value associated with the apparatus that can be used to move precisely define the orientation of the voltage/concentration curve.

4 Claims, 5 Drawing Sheets

PH AND CONCENTRATION METER

BACKGROUND OF THE INVENTION

1. Field of the Invention

The invention relates generally to the field of instrumentation for electrochemical measurement, and in particular to an improved meter for determining pH and concentration values for ionic solutions.

2. Description of the Related Art

Portable analytical instruments such as pH and concentration meters offer significant convenience to laboratory personnel, who must contend with a wide variety of experimental conditions and types of measurement. Typical metering arrangements include an ion-sensitive electrode that the user immerses in an electrolyte solution of interest, support circuitry, and display means for presenting to the user measurements of selected characteristics associated with ionic species in solution.

Currently available instrumentation includes meters capable of measuring hydrogen-ion concentration (generally in pH units) of aqueous solutions, absolute ion concentration (generally in units of equivalents/liter), dissolved oxygen concentration (generally in parts per million), and absolute or relative potential (generally in millivolts, and used in potentiometric titrations). Meters may be configured for visual display only, or adapted for interface to portable printers or even standalone computers.

Despite the versatility of such instrumentation, considerable effort on the part of the manufacturer is often required for assembly, and the units are not always convenient to operate. Conventional analytical electrodes consist of immersible glass tubing assemblies connected by wires to the analytical instrument. The electrode is usually first placed into the sample solution, and the meter subsequently positioned for reading. Repetition of this two-step procedure can cause wires to become dislodged in the course of experimental work, or result in electrode breakage if the metering apparatus is suddenly moved. Users also often misplace electrodes upon disengagement thereof from the apparatus.

Conventional packaging for metering instruments is often more expensive than necessary, because designers tend to neglect component interrelationships that can be exploited to facilitate modular assembly. For example, circuit boards, output ports, power supply and display components are often independently bolted into the main housing at various unrelated points, requiring separate installation operations for each.

A fundamental operational requirement of all electrochemical measurement instruments is user-performed calibration, which readies the meter for each use. Calibration is generally accomplished by sequentially immersing the electrode in each of a group of "reference solutions" of known pH or ionic concentration values and having temperature levels similar to those of the electrolyte solutions that will be measured. The current flows sensed by the meter as the electrode is introduced into each reference solutions are used as data points to orient a calibration curve that relates current flow to pH or concentration. This curve, based on the well-known Nernst equation, has a known, characteristic shape. With the dimensions and location of the calibration curve established by the reference measurements, values for pH or concentration can be obtained from the observed current flows obtained by immersing the electrode in solutions of interest.

One limitation associated with many known calibration systems is the narrow range of values along the curve that may be used as data points for curve orientation. The narrower the range of reference values, the less reliable will be the resulting calibration curve due to ambiguities in its orientation. A second limitation relates to noise associated with the meter circuitry itself which, if not accounted for during calibration, can jeopardize the validity of measurements.

DESCRIPTION OF THE INVENTION

Objects of the Invention

Accordingly, it is an object of the invention to provide an electrochemical metering apparatus that offers a high degree of operational convenience.

Another object of the invention is to provide an electrochemical metering apparatus that requires minimal assembly time.

A further object of the invention is to provide an electrochemical metering apparatus that facilitates highly accurate calibrations.

BRIEF SUMMARY OF THE INVENTION

The present invention comprises an electrochemical metering apparatus that provides for convenient storage and presentation of the analytical electrode, simple assembly, and two calibration modes.

The electrode storage and presentation assembly of the present invention comprises a ring-shaped support disposed on the main housing, which permits the user to introduce the electrode into a sample solution while simultaneously observing the meter's output. When not in use, the electrode may be conveniently stored in a compartment integral with the housing. The invention also comprises a foldable support assembly that facilitates angular orientation of the main housing.

The component parts of the invention are designed in a modular form for ease of assembly. All structural components are intended to fit together with interlocking tabs and windows. A serial port fits within the construction of the main housing without the need for bolts, and battery clips that depend directly from the circuit board obviate the need for wiring connections.

The present invention features two calibration modes. A "segment addition" mode permits separation of the voltage/concention curve into individually plotted regions, the number of which depends on the number of reference solutions used in the calibration procedure. The segment corresponding most closely to the measured potential of a sample solution is used to calculate concentration.

In an alternative calibration mode, one or more reference solutions are used to establish metered voltage/concentration combinations that are compared with expected, known values. Any discrepancies therebetween furnish a "noise level" value associated with the apparatus that can be used to more precisely define the orientation of the voltage/concentration curve.

BRIEF DESCRIPTION OF THE DRAWINGS

The foregoing discussion will be understood more readily from the following detailed description of the invention, when taken in conjunction with the accompanying drawings, in which.

DETAILED DESCRIPTION OF THE INVENTION

Figure 1:
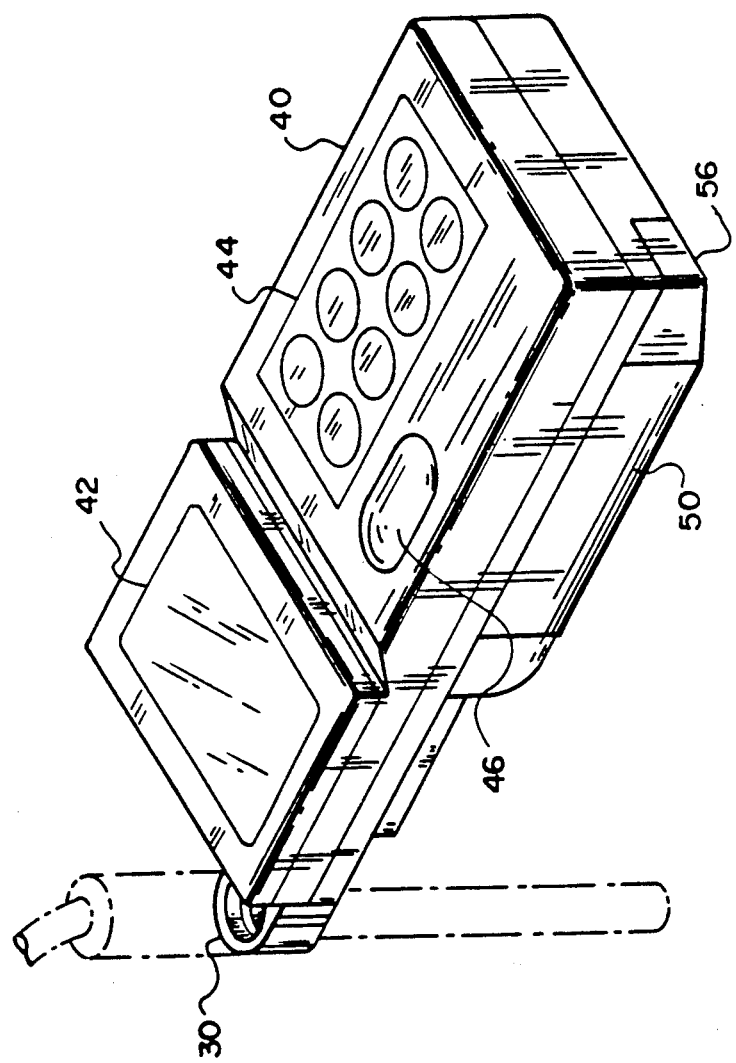
FIG. 1 is an isometric view of the present invention in assembled form.
Figure 2:
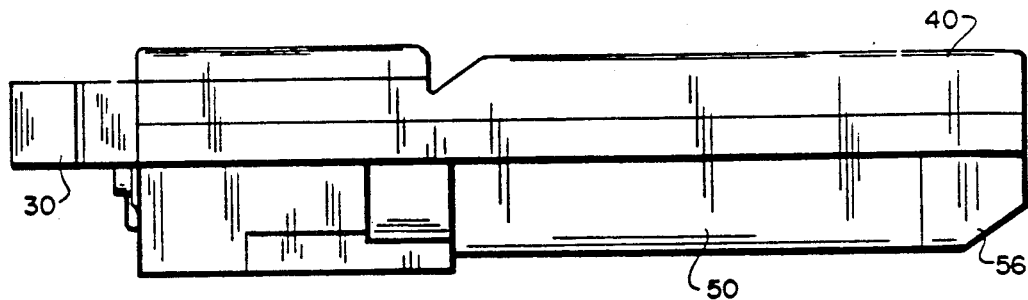
FIG. 2 is an elevational view of the present invention in assembled form, taken from the left side.
Figure 3:
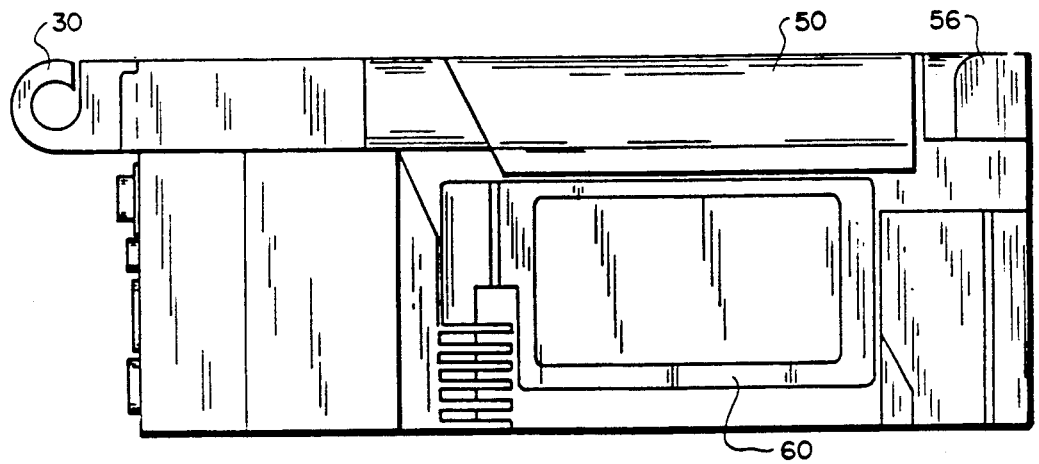
FIG. 3 is a bottom view of the present invention in assembled form.
Figure 4:
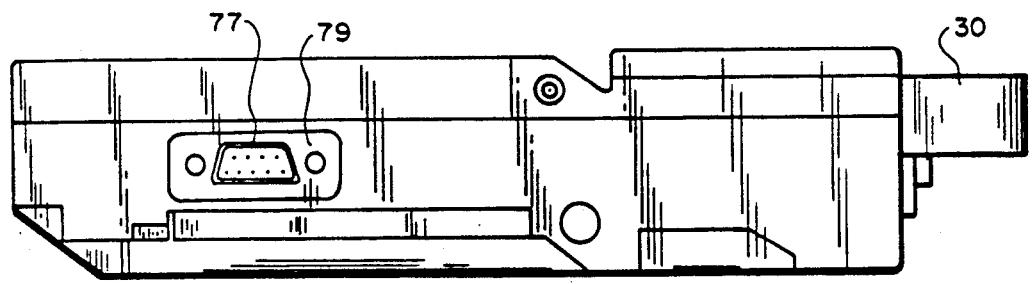
FIG. 4 is an elevational view of the present invention in assembled form, taken from the right side.
Figure 5:
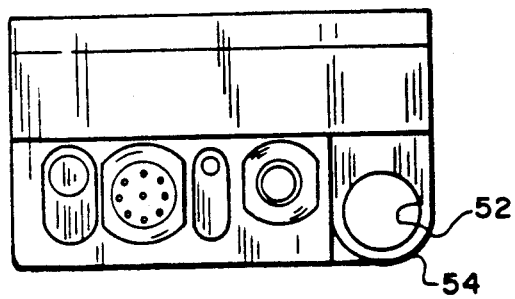
FIG. 5 is an elevational view of the present invention in assembled form, taken from the front.
Figure 6:
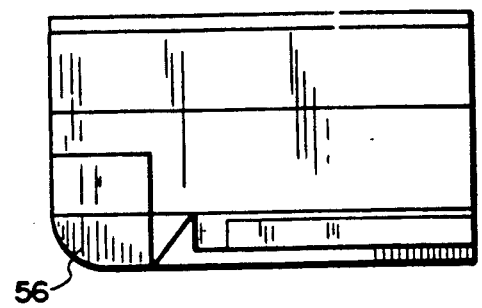
FIG. 6 is an elevational view of the present invention in assembled form, taken from the rear.

FIGS. 1-8 illustrate the novel mechanical features of the present invention. As shown in FIG. 1, the basic device is an electrochemical metering apparatus that comprises a housing 40, display 42 and keypad 44. Contained within housing 40 (and not shown) is suitable support circuitry, some of which will be described in greater detail hereinbelow, for converting potential differences detected by an electrode into concentration or pH units based on the well-known Nernst equation. The keys of keypad 44 permit the user to select various different modes of operation, as are standard in the art.

Figure 8:
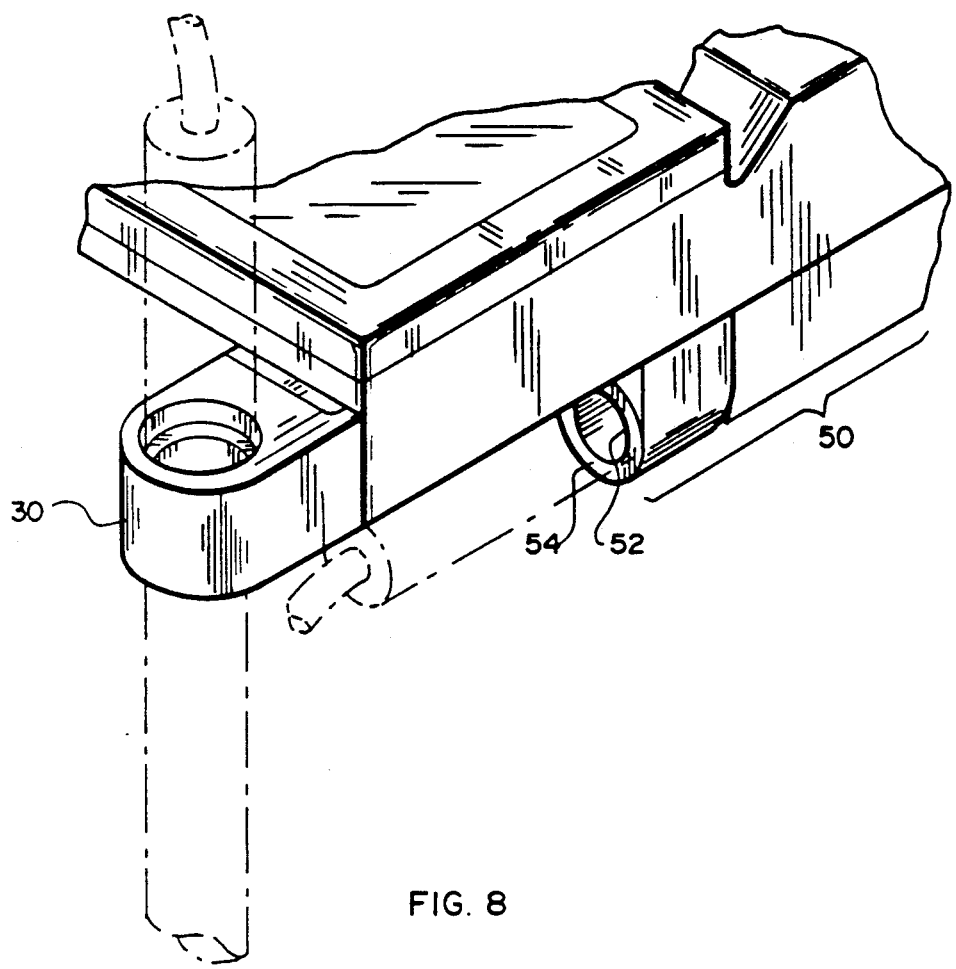
FIG. 8 is a detail of the electrode storage and presentation assembly.

Refer now to FIGS. 1 and 8, which show a ring-shaped support 30 that is snapped into or otherwise disposed on housing 40, and which admits an electrode (shown in ghost in FIG. 1). The diameter of support 30 is approximately equal to that of a standard electrode barrel, such that when an electrode is slidably introduced therein, it will come to rest when its cap meets the top of support 30. The electrode will also not exhibit lateral movement if the diameter of support 30 is well-chosen. This configuration permits convenient presentation of the electrode to a container of electrolyte solution during the metering operation, and allows the user to retain, in one hand, both the instrument and the electrode as a single unit. Thumb rest 46, which can be a depression molded into housing 40, further contributes to the user's comfortable grip when handling the apparatus.

To facilitate convenient storage of the electrode when not in use, the invention also features a storage compartment 50 having an axial bore 52 of diameter approximately equal to that of a standard electrode barrel. The electrode is introduced into bore 52 through aperture 54 (see FIG. 8). At the opposite of storage compartment 50 is a removable stopper 56 which, when in place, maintains the electrode in a moist condition. When stopper 56 is disengaged from storage compartment 50, bore 52 may be flushed to remove any solidified material that has accumulated therein.

Figure 7:
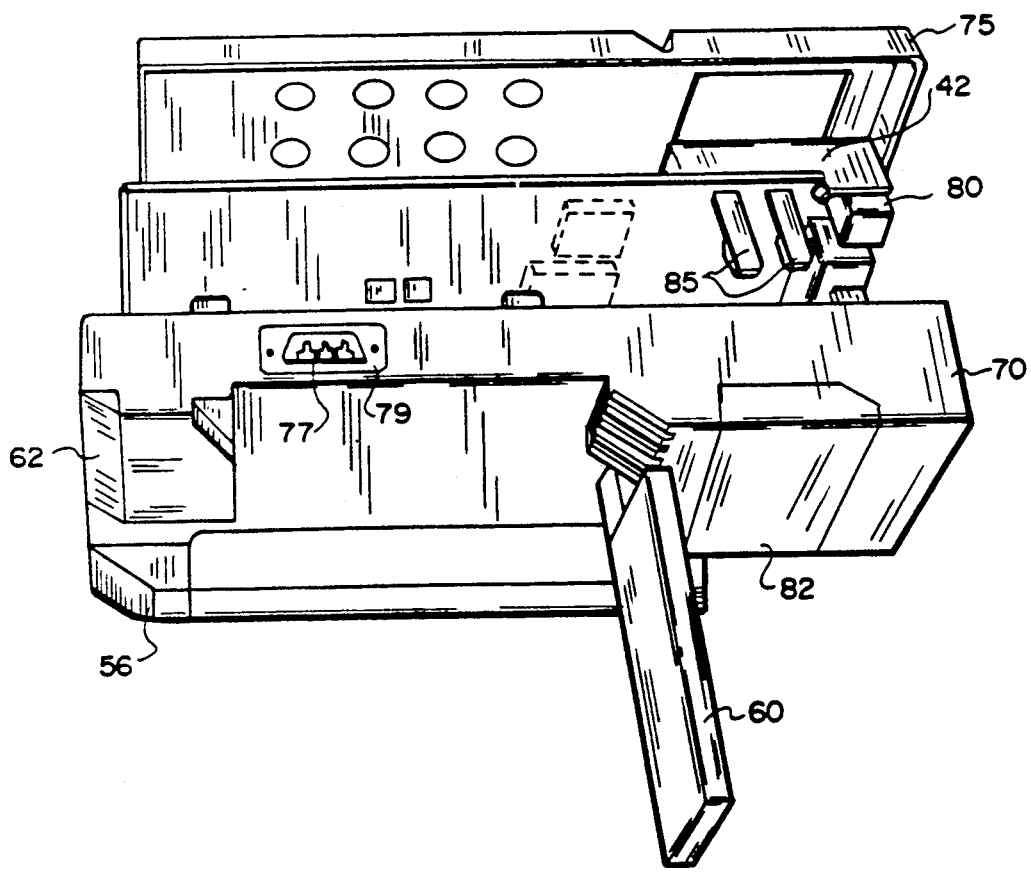
FIG. 7 is an exploded view of the various components of the present invention.

FIG. 7 illustrates another feature of the invention, namely, a foldable support assembly. This assembly comprises a support member 60 that is attached to bottom housing component 70 by means of a hinge. The hinge permits support member 60 to rotate from a rest position against bottom housing member 70 through an arc, until arriving at the extended position depicted in FIG. 7. When in the rest position, support member 60 fits snugly within a complementary depression in bottom housing member 70. Frictional member 62, which may be fabricated of rubber or other suitable material, is disposed at the forward end of bottom housing member 70. When support member 60 is extended and the device rested on a flat surface, frictional member 62 helps prevent movement of the device (e.g., as a consequence of the user pressing the keys of keypad 44).

The apparatus of the present invention is designed to permit rapid and convenient assembly of its component parts. All structural components may be fabricated of injection-molded plastic with interlocking tabs and windows. As shown in the exploded view of FIG. 7, the housing denoted by reference numeral 40 in FIG. 1, actually consists of bottom and top housing, components 70 and 75, respectively. Disposed therebetween is a printed circuit board 80, on which is mounted display 42 and the various electronic support circuitry necessary for operation. This support circuitry converts analog signals received from the electrode into digital form, and performs calculations thereon to produce a value for the concentration or pH parameter selected by the user. This value is ultimately converted into driver signals that direct presentation of the value on display 42.

The value may also be communicated to external devices through serial port 77, which preferably comprises an RS-232 connector having mounting tabs and a set of conductive prongs. Using the standard RS-232 protocol, the support circuitry can provide to external devices both the digitized potential value sensed by the electrode and the derived numerical result. Serial port 77 is fitted through aperture 79 and the mounting tabs thereof held in place by printed circuit board 80. Recall that housing members 70 and 75 are held together by interlocking tabs and windows, thereby securing circuit board 80 in a fixed position, which permits circuit board 80 to buttress serial port 77 against the inner wall of bottom housing member 70 without the need for bolts.

Figure 10:
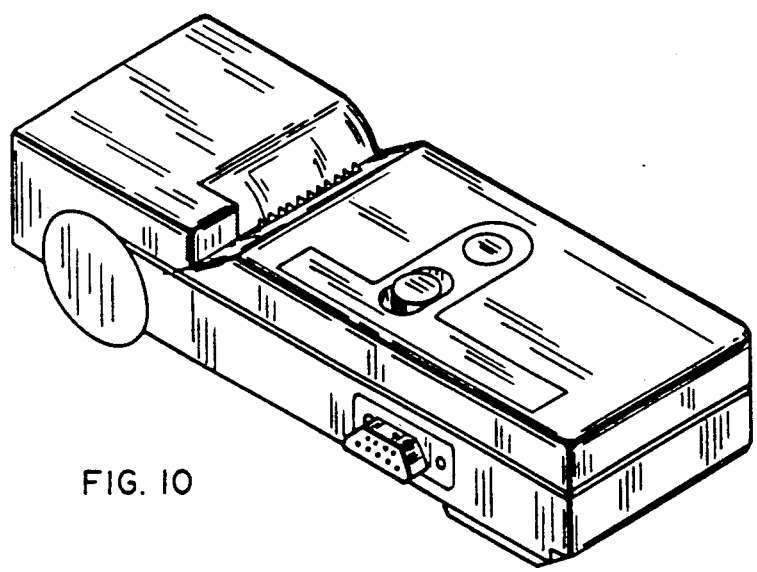
FIG. 10 is a perspective view of a printing device suitable for use in conjunction with the present invention.
Figure 11:
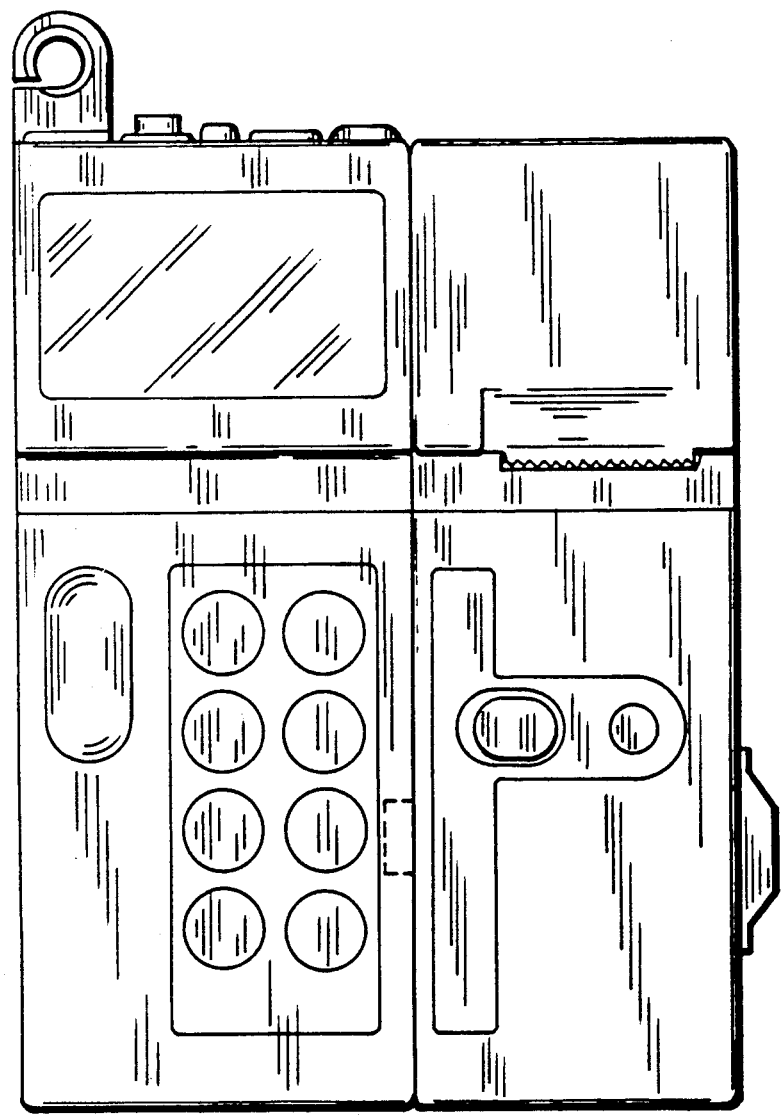
FIG. 11 is a plan view of the present invention in combination with the printer shown in FIG. 10.

Serial port 77 can be used, for example, to attach the apparatus of the present invention to an external printer. As shown in FIGS. 10 and 11, such a printer can be designed with dimensions similar to that of the measurement apparatus and equipped with a complementary serial port.

The components of circuit board 80 are powered by a battery that fits within a suitably shaped depression within bottom housing member 70. This depression is covered by removable plate 82. Contacts 85, which depend directly from circuit board 80, engage the battery terminals and conduct electricity to circuit board 80. Terminals 85 fit through apertures in the battery depression.

The apparatus further comprises a novel calculation and calibration module, distributed within a series of components (as will be hereinafter described) situated on circuit board 80, that facilitates precise measurements. Electrochemical measurements are typically performed according to the Nernst equation which, in its base-10 logarithmic form, is as follows:

$$E = E_0 + (2.303RT/nF)\log(C/C_{iso}) \quad \text{[Eq. 1]}$$

where E (usually the independent variable whose value is measured by an electrode immersed in the electrolytic solution of interest) is voltage, $E_0$ is the standard cell potential; R is the ideal gas constant; T is temperature in degrees Kelvin; n is the number of electrons transferred in the oxidation-reduction reactions occurring between the electrode and the sample solution; F is the Faraday constant; C is the equivalent ion concentration (usually the dependent variable to be calculated); and $C_{iso}$ (the isopoint concentration) is the concentration at which the electrode exhibits no temperature response.

Eq. 1 can be rewritten to accomodate measurements in degrees Centrigade as follows:

$$E = E_0 + (2.303R \cdot 298.15/nF)([t+273.15]/298.15) \log(C/C_{iso}) \quad [\text{Eq. 2}]$$

where t is temperature in degrees Centigrade. Abbreviating the first parenthetical term as k, which represents the slope dE/d(log C) at 25 degrees Centigrade, and solving for $E_0$, Eq. 2 becomes $$E_0 = E - k([t+273.15]/298.15)\log(C/C_{iso}) \quad [\text{Eq. 3}]$$

Although the curve specified by Eqs. 1 and 2 has a characteristic shape, its orientation naturally depends on the value of $E_0$. The standard method of obtaining a value for $E_0$ is to immerse the electrode in a solution of known temperature and concentration, and then use Eq. 3 to calculate $E_0$. Unfortunately, due to the imprecision of electrochemical measuring devices, the Nerst equation does not always return completely accurate values. It is possible, for example, for internal metering characteristics to cause changes in sensitivity over the range of measured voltages, thereby producing concentration values that deviate from true according to the magnitude of the sensed voltage.

In order to enhance the accuracy of measurements, the present invention permits the user to establish baseline $E_0$ values for several reference solutions having different known electrochemical potentials. The $E_0$ value derived from a reference potential close to that of a sample's measured potential can be used to calculate its concentration, thereby "fine tuning" the Nernst equation to the sample's potential. More precisely, the curve specified by Eq. 1 or 2 is segmented into regions lying between the known values of the reference solutions. When the user introduces the electrode into a solution of unknown concentration, the invention first determines the region within which the measured potentials fits. The invention then retrieves the associated $E_0$ value, and proceeds to calculate the concentration according to Eq. 1 or 2.

The value of $E_0$ between points is calculated according to the following equations:

$$k = (298.15 \cdot [E_{std1} - E_{std2}])/([273.15+t_1] \cdot \log[C_1/C_{iso}] - [273.15+t_2] \cdot \log[C_2/C_{iso}]) \quad [\text{Eq. 4}]$$

where $E_{std1}$ and $E_{std2}$ are known potential values for two standard reference solutions, $t_1$ and $t_2$ are corresponding temperature measurements of these solutions, and $C_1$ and $C_2$ are the concentrations. $E_0$ can then be calculated according to either of the equations $$E_0 = E_1 - k([273.15+t_2]/298.15)\log(C_2/C_{iso}) \quad [\text{Eq. 5a}]$$

$$E_0 = E_2 - k([273.15+t_1]/298.15)\log(C_1/C_{iso}) \quad [\text{Eq. 5b}]$$

where $E_1$ and $E_2$ are the measured potentials of the reference solutions.

Figure 9:
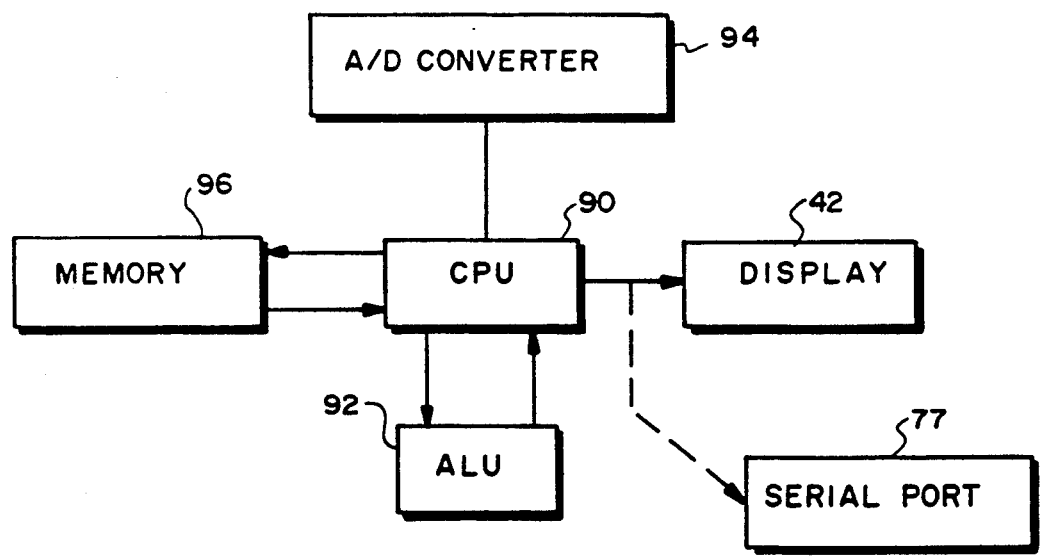
FIG. 9 is a schematic representation of the various components of the calculation and calibration module.

The calculation and calibration module are shown schematically in FIG. 9. The module comprises a central-processor unit (CPU) 90 which cooperates with an arithmetic and logic unit (ALU) 92 to receive input and perform calculations. CPU 90 receives input information from an analog-to-digital (A/D) converter 94, which itself receives analog signals directly from the electrode. A memory bank 96 holds the instructions and "scratchpad" registers necessary for CPU 90 and ALU 92 to perform the requisite calculations; it also retains values for the known equivalent ion concentrations and potentials of the reference solutions. After calculations have been performed, CPU output is transferred to display 42 and, possibly, to serial port 77.

Accordingly, the user first establishes $E_0$ values for the reference solutions by entering the known concentration and voltage values and taking actual voltage measurements. These values are stored in memory 96. When the electrode is immersed in a solution of unknown concentration, CPU 90 and ALU 92 perform comparison operations with the values in memory 96 to determine which reference potential exceeds the newly measured value by the least amount. The $E_0$ value associated with this reference potential is used to calculate the concentration of the sample solution according to Eq. 1 or 2.

Another approach to calibration offered by the present invention assumes that the deviations in $E_0$ along the Nernst curve are due to a constant noise value associated with the measurement apparatus. This value can then be derived by comparing potential values obtained for one or more reference solutions with the known potential values for those solutions. Such an approach is useful where the Nernst curve "bottoms out", i.e., where the voltage response to differences in concentration is too small for ordinary calibration procedures. This procedure has been found particularly useful where the measured differences among three reference solutions do not exceed 10 millivolts.

Thus, modifying Eq. 3 to account for the adjustment parameter (denoted as A), $$E_0 = E - k([t+273.15]/298.15)\log([C+A]/C_{iso}) \quad [\text{Eq. 6}]$$

If more than one reference solution is employed, individual derived adjustment values can be averaged, or an intermediate adjustment value that minimizes differences among the $E_0$ values established using regression techniques.

Alternatively, A can be derived by immersing the electrode into a distilled water solution and obtaining the measurement registered by the metering apparatus. This deviation from the expected value of zero can be used to calculate A according to Eq. 6.

Thus, instead of segmenting the Nernst curve into regions, this form of calibration uses one or more measurement points to redefine the overall equation, which is then used for calculation at any measured potential.

The terms and expressions which have been employed are used as terms of description and not of limitation, and there is no intention, in the use of such terms and expression, of excluding any equivalents of the features shown and described or portions thereof, but it is recognized that various modifications are possible within the scope of the invention claimed.

We claim:

1. An electrochemical metering apparatus that facilitates one-handed operation, comprising:
   a. a display means disposed in a housing;
   b. electrode means for quantitatively detecting at least one characteristic associated with ionic species in solution, which electrode means is operatively connected to said display means to cause display of at least one quantity representative of the at least one characteristic; and
   c. a ring-shaped support disposed on the exterior of the housing for slidably and removably receiving the electrode therein and facilitating presentation of the received electrode to a sample.

2. The electrochemical metering apparatus of claim 1 further comprising a thumb rest integral with the housing that facilitates a firm one-handed grip thereon.

3. The electrochemical metering apparatus of claim 1 further comprising electrode storage means which itself comprises:
   a) a tube integral with the housing and having a diameter closely approximating that of the electrode to facilitate a snug fit therebetween; and
   b) a removable stopper disposed at the end of the tube.

4. The electrochemical metering apparatus of claim 3 further comprising a foldable support attached to the housing by means of a hinge, and frictional means for discouraging movement of the housing when the support is engaged.

* * * * *